United States Patent
Liu et al.

(10) Patent No.: US 11,439,787 B2
(45) Date of Patent: Sep. 13, 2022

(54) PORTABLE AIR FILTRATION AND DISINFECTION DEVICE FOR A RESPIRATOR SYSTEM

(71) Applicants: Haiping Liu, Shenzhen (CN); Yang Michelle Sun, Moraga, CA (US)

(72) Inventors: Haiping Liu, Shenzhen (CN); Yang Michelle Sun, Moraga, CA (US)

( * ) Notice: Subject to any disclaimer, the term of this patent is extended or adjusted under 35 U.S.C. 154(b) by 327 days.

(21) Appl. No.: 16/865,306

(22) Filed: May 2, 2020

(65) Prior Publication Data

US 2021/0268319 A1    Sep. 2, 2021

(51) Int. Cl.
*A61M 16/10*   (2006.01)
*A62B 23/02*   (2006.01)
*A62B 23/06*   (2006.01)
*B01D 46/00*   (2022.01)
*B01D 47/02*   (2006.01)
*B01D 50/60*   (2022.01)

(52) U.S. Cl.
CPC ...... *A61M 16/1065* (2014.02); *A61M 16/107* (2014.02); *A62B 23/02* (2013.01); *A62B 23/025* (2013.01); *A62B 23/06* (2013.01); *B01D 46/0028* (2013.01); *B01D 46/0036* (2013.01); *B01D 47/021* (2013.01); *B01D 50/60* (2022.01); *A61M 2205/7509* (2013.01); *A61M 2205/7518* (2013.01); *A61M 2205/7536* (2013.01); *A61M 2205/7545* (2013.01); *B01D 2279/65* (2013.01)

(58) Field of Classification Search
CPC ............ A61M 16/1065; A61M 16/107; A61M 2205/75; A61M 2205/7509; A61M 2205/7518; A61M 2205/7536; A62B 23/02; A62B 23/025; A62B 23/06; B01D 50/60; B01D 46/0028; B01D 46/0036; B01D 46/12; B01D 47/021; A61L 2209/21; A61L 2209/211
See application file for complete search history.

(56) References Cited

U.S. PATENT DOCUMENTS

| | | | |
|---|---|---|---|
| 6,616,733 B1* | 9/2003 | Pellegrin | B01D 47/021 96/279 |
| 2010/0269828 A1* | 10/2010 | Orr | A61M 16/0093 128/205.12 |
| 2014/0261416 A1* | 9/2014 | Arcilla | A61M 16/0891 128/203.14 |
| 2018/0015310 A1* | 1/2018 | Choi | A62B 25/00 |

* cited by examiner

*Primary Examiner* — Robert Clemente
(74) *Attorney, Agent, or Firm* — Jigang Jin

(57) ABSTRACT

A portable air filtration and disinfection device for a respirator system includes a casing, an inhalation filter assembly, and an exhalation filter assembly. The inhalation filter assembly includes an intake duct for receiving breathing air, an inhalation gas filter for filtering the breathing air, and an inhalation duct to provide the filtered breathing air. The exhalation filter assembly includes an exhalation duct for receiving exhaled air, an exhalation gas filter and an exhalation liquid filter for filtering and disinfecting the exhaled air, and an outlet duct for releasing the filtered and disinfected exhaled air.

20 Claims, 6 Drawing Sheets

PORTABLE AIR FILTRATION AND DISINFECTION DEVICE FOR A RESPIRATOR SYSTEM

CROSS-REFERENCE TO RELATED APPLICATION

This application claims priority to Chinese patent application No. 202020234914.5, filed Feb. 28, 2020, the entire content of which is incorporated herein by reference.

FIELD OF INVENTION

This invention generally relates to air filtering apparatus and specifically to respirators.

BACKGROUND OF THE INVENTION

Respirators are capable of filtering air to reduce the presence of certain substances, e.g., microbes and particulates. When a user wears a respirator to cover the nose and mouth, the respirator not only prevents impurities or contaminants from entering the user's breathing air, but also protects the user and other people from being exposed to the contaminants exhaled by the user.

A respirator includes a filtering structure or replaceable filtration cartridge that includes one or more filter layers. Contaminants such as dusts, mists, fumes, viruses, and/or microbes are the targets to be filtered by a respirator. A filter layer may include a mesh material that is sufficiently breathable and strong. In addition, a filter layer may also include an adsorption media that adsorbs hazardous or odorous gases.

In a hospital where individuals may be exposed to hazardous gases, vapors, dusts, mists, viruses, and biological agents, respirators with improved filtration and adsorption capabilities are desirable. Disinfection of the breathing air and the exhaled air is also desirable. However, conventional respirators do not disinfect the air that passes through them. Thus, patients re-breath in the viruses they exhaled into the external environment (e.g., ICU room) or trapped in their masks.

Liquid can be used to filter the air by removing particulate matter and toxic gases from it. When air is filtered by disinfection liquid, the air can be cleaned and disinfected. However, a conventional air filtration system that utilizes liquid as filter is often bulky, heavy, installed in a building, e.g., at an industrial site, and not suitable for personal use or wearable applications.

Therefore, there exists a need for a respirator with improved filtering and disinfection capabilities, and a respirator with liquid filtration.

SUMMARY OF THE INVENTION

The present invention discloses a portable air filtration and disinfection device that can be used in a respirator system. In one embodiment, the portable air filtration and disinfection device includes a casing, an inhalation filter assembly, and an exhalation filter assembly. The casing has a first chamber and a second chamber that house the inhalation filter assembly and the exhalation filter assembly, respectively. The inhalation filter assembly includes an intake duct for receiving air from an external environment or source, an inhalation gas filter for filtering the received air from the external environment or source, and an inhalation duct to provide the filtered air to a person for breathing. The exhalation filter assembly includes an exhalation duct for receiving air exhaled by the person, an exhalation gas filter and an exhalation liquid filter for filtering and disinfecting the received exhaled air from the person, and an outlet duct for releasing the filtered and disinfected exhaled air to the external environment or source.

In another aspect, the portable air filtration and disinfection device includes an inhalation filter assembly, an exhalation filter assembly, and a casing. The inhalation filter assembly includes an intake duct for receiving air from an external environment or source, an inhalation gas filter for filtering the received air from the external environment or source, and an inhalation duct connected with a mask for providing the filtered air to a person for breathing via the mask. The exhalation filter assembly includes an exhalation duct connected with the mask for receiving air exhaled by the person via the mask, an exhalation gas filter and an exhalation liquid filter for filtering and disinfecting the received exhaled air from the person, and an outlet duct for releasing the filtered and disinfected exhaled air to the external environment or source. The casing houses the inhalation filter assembly and the exhalation filter assembly.

In another aspect, the portable air filtration and disinfection device includes a casing, an inhalation filter assembly, and an exhalation filter assembly. The casing has two chambers that house the inhalation filter assembly and the exhalation filter assembly. The inhalation filter assembly includes an intake duct connected with a ventilator for receiving air from the ventilator, an inhalation gas filter for filtering the received air from the ventilator, and an inhalation duct to provide the filtered air to a person for breathing. The exhalation filter assembly includes an exhalation duct for receiving air exhaled by the person, an exhalation gas filter and an exhalation liquid filter for filtering and disinfecting the received exhaled air from the person, and an outlet duct connected with the ventilator for releasing the filtered and disinfected exhaled air to the ventilator. Besides ventilators, the portable air filtration and disinfection device may be connected to and work with a PAPRA, CPAP, BIPAP, Nebulizer, or Oxygen delivery system.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings.

DETAILED DESCRIPTION

Detailed description of the present invention is provided below along with figures and embodiments, which further clarifies the objectives, technical solutions, and advantages of the present invention. It is noted that schematic embodiments discussed herein are merely for illustrating the invention. The present invention is not limited to the embodiments disclosed.

Figure 1A:
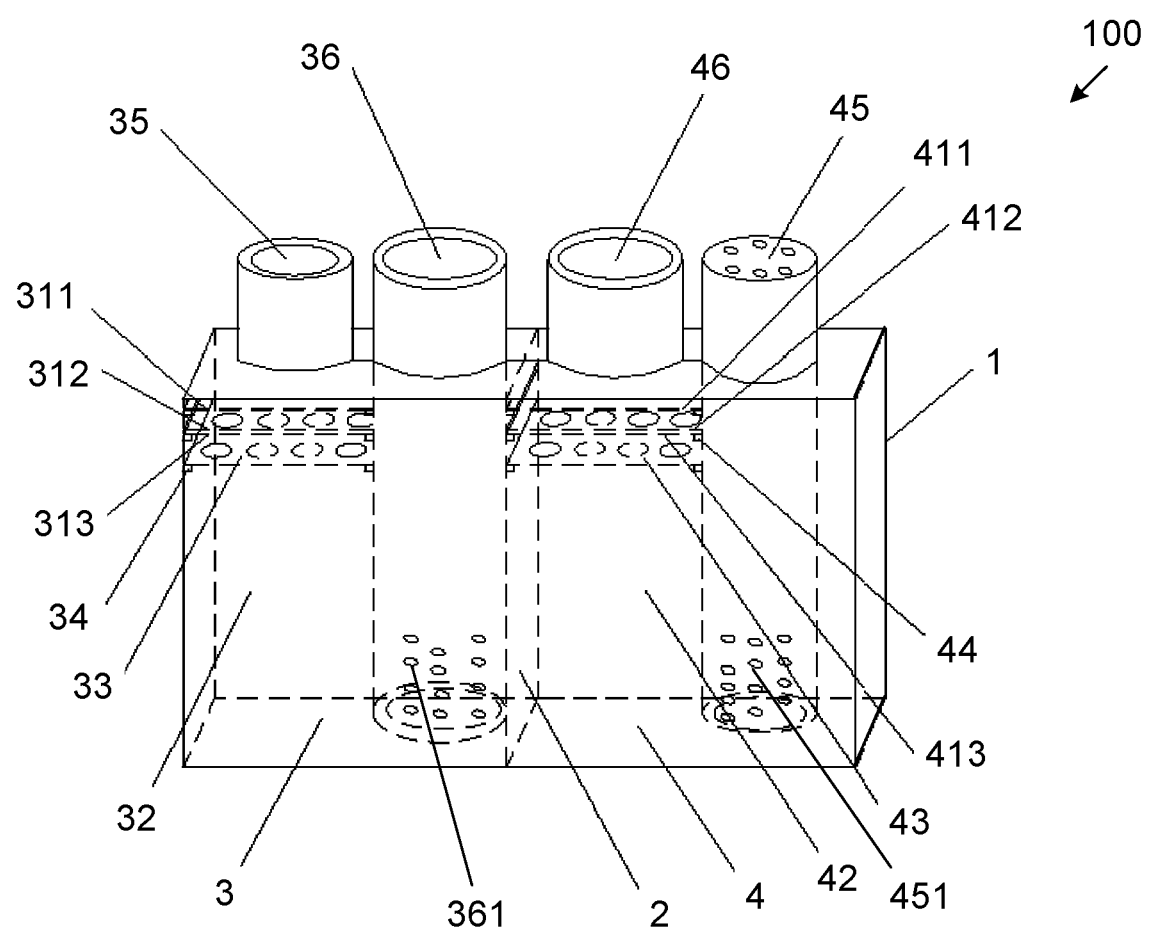
FIG. 1A schematically illustrates a perspective view of an exemplary portable air filtration and disinfection device, according to an embodiment of the present invention.
Figure 1B:
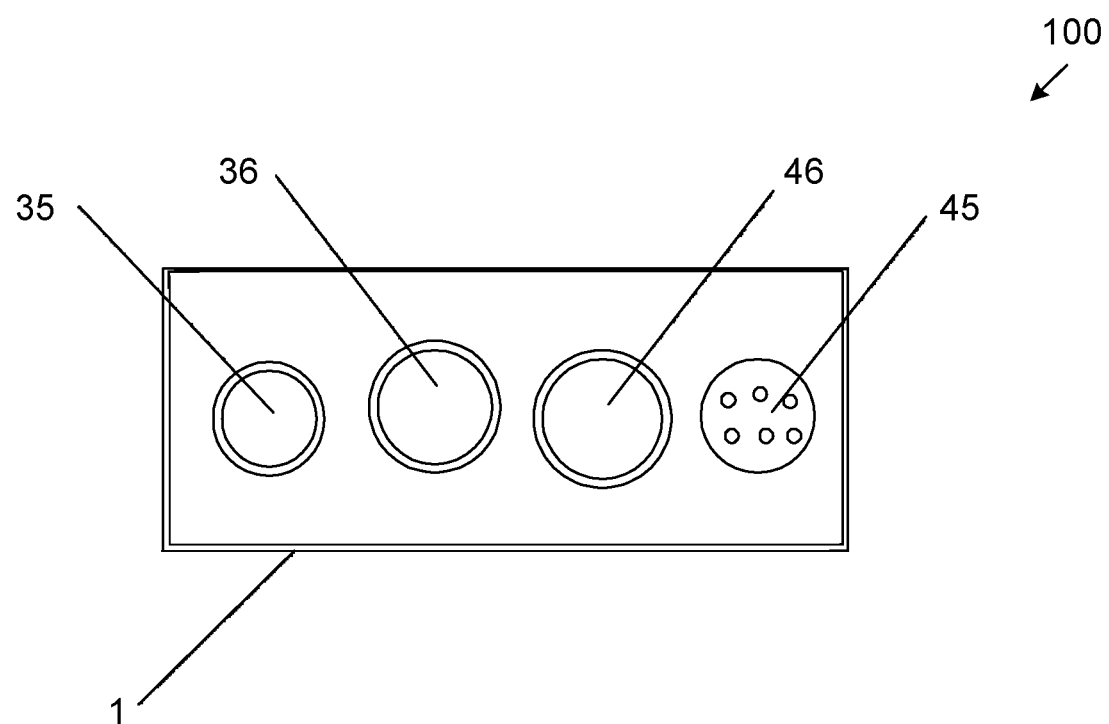
FIG. 1B schematically illustrates a top view of the portable air filtration and disinfection device shown in FIG. 1A.
Figure 1C:
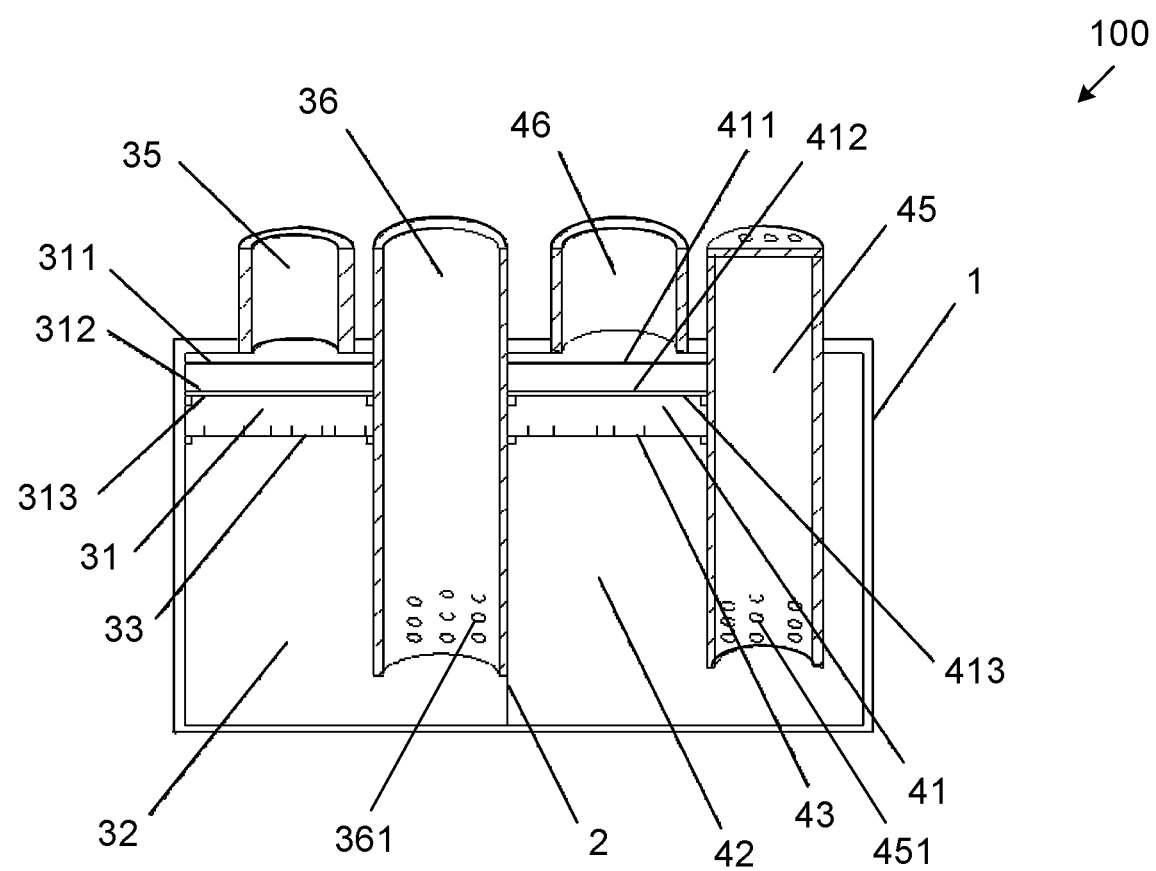
FIG. 1C schematically illustrates a cutaway view of the portable air filtration and disinfection device shown in FIGS. 1A and 1B.

FIGS. 1A, 1B, and 1C illustrate a portable air filtration and disinfection device 100 for a respirator system according to an embodiment of the present invention. FIG. 1A is a perspective view of the portable air filtration and disinfection device 100, while FIGS. 1B and 1C are a top view and a cutaway view, respectively. As shown in FIGS. 1A-1C, device 100 may include a casing 1 and a chamber spacer 2 that separates two chambers inside casing 1. The two chambers house an exhalation filter assembly 3 and inhalation filter assembly 4, respectively.

Exhalation filter assembly 3 may include an exhalation gas filter 31, an exhalation liquid filter 32, an exhalation filter plate 33, first bayonets 34, an outlet duct 35, and an exhalation duct 36. Exhalation filter plate 33 is disposed between exhalation gas filter 31 and exhalation liquid filter 32 and fastened by the first bayonets 34 on sidewalls of exhalation filter assembly 3. Outlet duct 35 is connected to exhalation gas filter 31, and exhalation duct 36 is provided on one side of exhalation liquid filter 32.

Inhalation filter assembly 4 may include an inhalation gas filter 41, an inhalation liquid filter 42, an inhalation filter plate 43, second bayonets 44, an intake duct 45, and an inhalation duct 46. Inhalation filter plate 43 may be disposed between inhalation gas filter 41 and inhalation liquid filter 42 and fastened by the second bayonets 44 on sidewalls of inhalation filter assembly 4. Inhalation duct 46 may be connected to inhalation gas filter 41, and intake duct 45 may be provided on one side of inhalation liquid filter 42.

Casing 1 may have a shape such as a rectangular shape or an oval shape and be made of a rigid and durable material such as a metal material or a plastic material, e.g., a polypropylene (PP) material. Exhalation gas filter 31 may include one or more filters, for example, a filter 311, a filter 312, and a filter 313 that are fastened by the first bayonets 34 on sidewalls of exhalation filter assembly 3. In some embodiments, filters 311-313 may be arranged in a top-down order in the vertical direction, as shown in FIG. 1C. In some other embodiments, filters 311-313 may be arranged in orders other than the described top-down order in the vertical direction. Inhalation gas filter 41 may also include one or more filters, for example, a filter 411, a filter 412, and a filter 413 that are fastened by second bayonets 44 on sidewalls of exhalation filter assembly 4. In some embodiments, filters 411-413 may be arranged in a top-down order in the vertical direction, as shown in FIG. 1C. In some other embodiments, filters 411-413 may be arranged in orders other than the described top-down order in the vertical direction. Exhalation filter plate 33 and inhalation filter plate 43 may be made from a plastic material, e.g., a PP material, or a material with similar performance.

Filters 311 and 411 may include one or multiple fabric layers of sufficiently breathable and strong materials, such as electrostatic non-woven polypropylene fiber. The one or multiple fabric layers may be configured to remove a high percentage of particulates and other contaminants from an air stream that passes through the one or multiple fabric layers.

Filters 312 and 412 may include one or multiple layers of sorptive materials, such as activated carbon. The sorptive materials may be configured to adsorb certain hazardous or odorous gases to remove or reduce the levels of the gases and odors.

Filters 313 and 413 may include one or multiple layers of filter mesh made from metal, rubber, nylon, plastic, etc. The size of the mesh may be selected to stop certain sizes of particles from passing through.

In some embodiments, filters 311-313 and 411-413 may be configured as discrete components that may be replaced individually. In some other embodiments, filters 311-313 may be packaged in a changeable filter cartridge (not shown) and filters 411-413 may be packaged in another changeable filter cartridge (not shown). Then, the filters may be replaced periodically or after certain events. For example, a side plate of casing 1 may be opened to expose the filters or filter cartridges. Hence, filters 311-313 and 411-413 may be replaced when needed.

Exhalation liquid filter 32 and inhalation liquid filter 42 may include a liquid such as a nontoxic disinfection liquid. As such, the nontoxic disinfection liquid not only filters particulates and gases in an air stream that passes through it, but also disinfects the air stream. For example, the nontoxic disinfection liquid may include vinegar water, hydrogen peroxide, chlorine dioxide, lactic acid, pine oil, citric acid, or other liquid disinfectant that has no or very low toxicity to human. The nontoxic disinfection liquid may be replaced periodically or after certain events. Exhalation liquid filter 32 and inhalation liquid filter 42 may include silicone or a composite material that may be used repeatedly after disinfection within a validity period.

When the portable air filtration and disinfection device 100 is engaged with a user, the breathing air enters intake duct 45 and is injected into the disinfection liquid through small holes 451 on the sidewall near the bottom of intake duct 45. The injected breathing air forms small bubbles that move upward through the liquid. In the interface of the small bubble and the liquid, particulates and gasses in the breathing air may be captured by the liquid, and the air in contact with the liquid may be disinfected by disinfectants in the liquid.

After the small bubbles reach the surface of the disinfection liquid of inhalation liquid filter 42, they release the air inside the bubbles. The breathing air, after filtered by the disinfection liquid, flows through inhalation gas filter 41 before exiting the portable air filtration and disinfection device 100 via inhalation duct 46. When the breathing air passes inhalation gas filter 41, it is filtered by filters 411-413 separately.

The exhaled air from a user's exhalation enters portable air filtration and disinfection device 100 via exhalation duct 36. The exhaled air is then injected into the disinfection liquid through small holes 361 on the sidewall near the bottom of exhalation duct 36. The injected exhaled air forms small bubbles that move upward through the liquid. In the interface of the small bubble and the liquid, particulates and gasses in the exhaled air may be captured by the liquid, and the air in contact with the liquid may be disinfected by disinfectants in the liquid.

After the small bubbles reach the surface of the disinfection liquid of exhalation liquid filter 32, they release the exhaled air inside the bubbles. The exhaled air, after filtered by the disinfection liquid, flows through exhalation gas filter 31 before exiting the portable air filtration and disinfection device 100 via outlet duct 35. When the exhaled air passes through exhalation gas filter 31, it is filtered by filters 311-313 separately.

Figure 2:
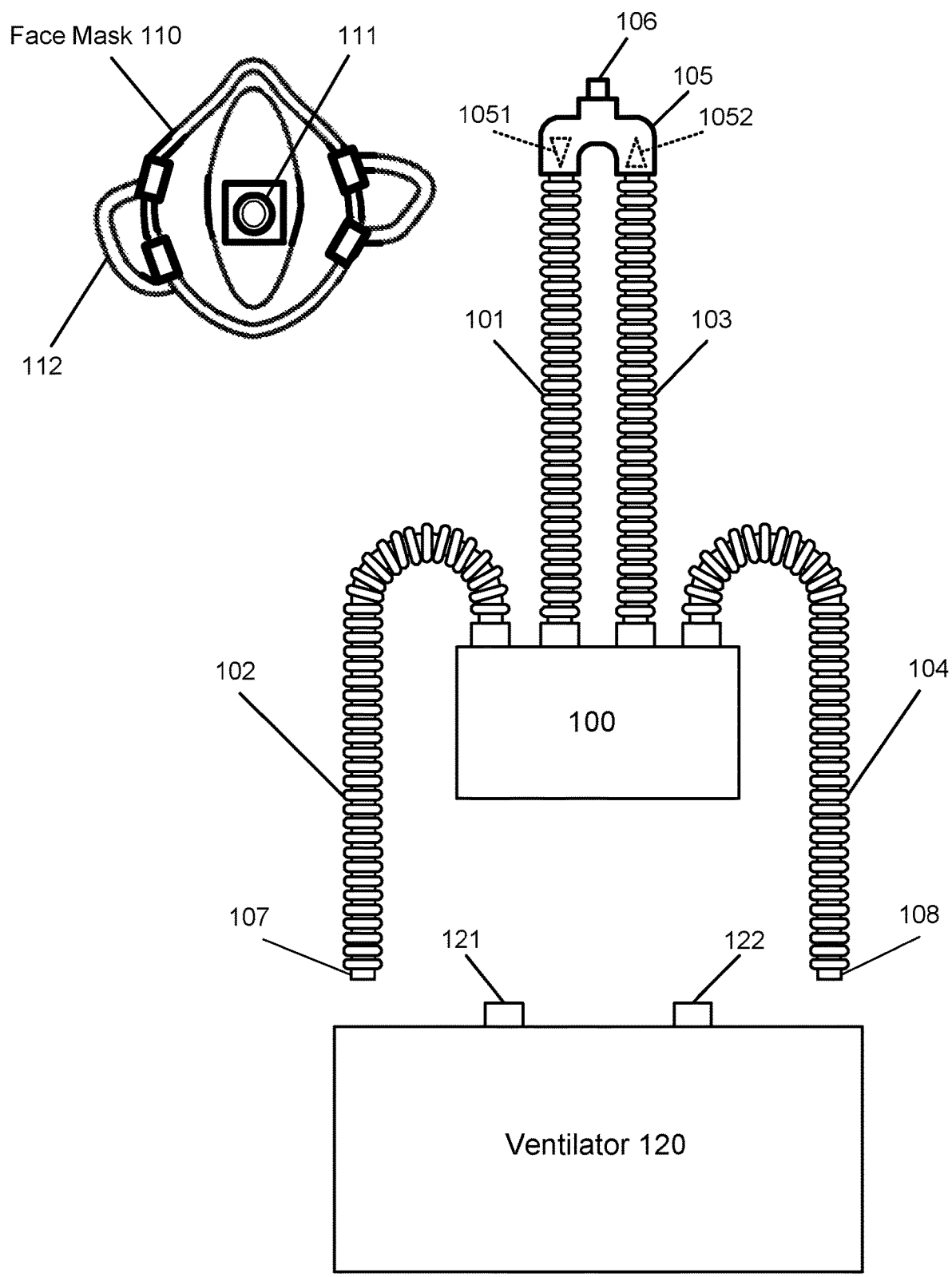
FIG. 2 illustrates a respirator system that includes a portable air filtration and disinfection device and a face mask, according to an embodiment of the present invention.

FIG. 2 illustrates a respirator system that includes a portable air filtration and disinfection device 100 and a face mask 110 according to an embodiment of the present invention. The respirator system works with a ventilator 120 for a patient. A "face mask", as used herein, may indicate a mask that has sufficient dimensions to cover a person's nose and mouth when worn. A ventilator is also called a mechanical ventilator or breathing machine. A ventilator is a pneumatic and electronics system that is designed to monitor, assist, and/or control pulmonary ventilation, and respiration intermittently or continuously. For example, a ventilator can take over the work of breathing when a patient is not able to breathe enough on his or her own. A ventilator contains an inspiratory line and an expiratory line that are coupled to a patient via a user interface, such as a face mask. The inspiratory line is used to provide the breathing air from an air supply device for a patient. The expiratory line is used to discharge the exhaled air from a patient.

The portable air filtration and disinfection device 100 may be respectively coupled with face mask 110 and ventilator 120 in a fluid-communicating manner. As shown in FIG. 2, face mask 110 may have a cup-shaped configuration and include a tube port 111 and a mask strap 112. In some other embodiments, face mask 110 may be replaced by a nasal mask (not shown) that covers a patient's nose or a mouth piece (not shown) that is inserted into a patient's mouth. Compared to the embodiment shown in FIGS. 1A-1C, the portable air filtration and disinfection device 100 shown in FIG. 2 may further include flexible tubes that form exhalation branches 101 and 102 and inhalation branches 103 and 104. Branches 101 and 103 are connected to a Y-connecter 105 that has a connector 106. Connector 106 may be detachably coupled to tube port 111 of mask 110.

Inside Y-connector 105, there may be two one-way directional valves 1051 and 1052. During exhalation, the exhaled air may be released from mask 110 into exhalation branch 101 via valve 1051, while valve 1052 blocks exhalation to inhalation branch 103. During inhalation, the breathing air flows to mask 110 from inhalation branch 103 via valve 1052, while valve 1051 blocks the air from exhalation branch 101. Thus, because the inhalation filter assembly and the exhalation filter assembly are separate and also because of the separate flexible tubes and the one-way directional valves, the exhaled air from the mask 110 will not be travel back to the mask and re-breathed by the patient wearing the mask, preventing the patient from re-breathing any viruses he/she exhaled into the device. In some other embodiments, one-way directional valves 1051 and 1052 may not be integrated with Y-connector 105. Instead, valves 1051 and 1052 may be discrete devices that may be coupled with branches 101 and 103 separately and individually.

Exhalation branch 101 is connected with an exhalation duct of the portable air filtration and disinfection device 100, such as exhalation duct 36, to filter the exhaled air. The filtered exhaled air, after the liquid filtration and the gas filtration, is released into exhalation branch 102 via an outlet duct, such as outlet duct 35. Exhalation branch 102 may be connected with ventilator 120. For example, a tube end 107 of branch 102 may be coupled detachably with a tube port 121 that may be connected with an expiratory line (not shown) of ventilator 120. Thus, the exhaled air may be discharged into ventilator 120 via exhalation branches 101 and 102 and the expiratory line.

Inhalation branch 103 is connected with an inhalation duct of device 100, such as inhalation duct 46. An intake duct of device 100, such as intake duct 45, is connected with inhalation branch 104. Inhalation branch 104 may be connected with ventilator 120. For example, a tube end 108 of branch 104 may be coupled detachably with a tube port 122 that may be connected with an inspiratory line (not shown) of ventilator 120. During inhalation, the breathing air flows from ventilator 120 to device 100 via the inspiratory line, tube port 122, and inhalation branch 104. Then the filtered breathing air, after the liquid filtration and the gas filtration, flows to mask 100 via inhalation branch 103.

Hence, by combining a liquid filtration system and a gas filtration system, the respirator system may not only disinfect the breathing air and remove harmful substances from the breathing air, but also disinfect and filter the exhaled air at the same time. As such, it reduces the contamination of the exhaled air in the surrounding environment while cleaning the inhaled air.

Figure 3:
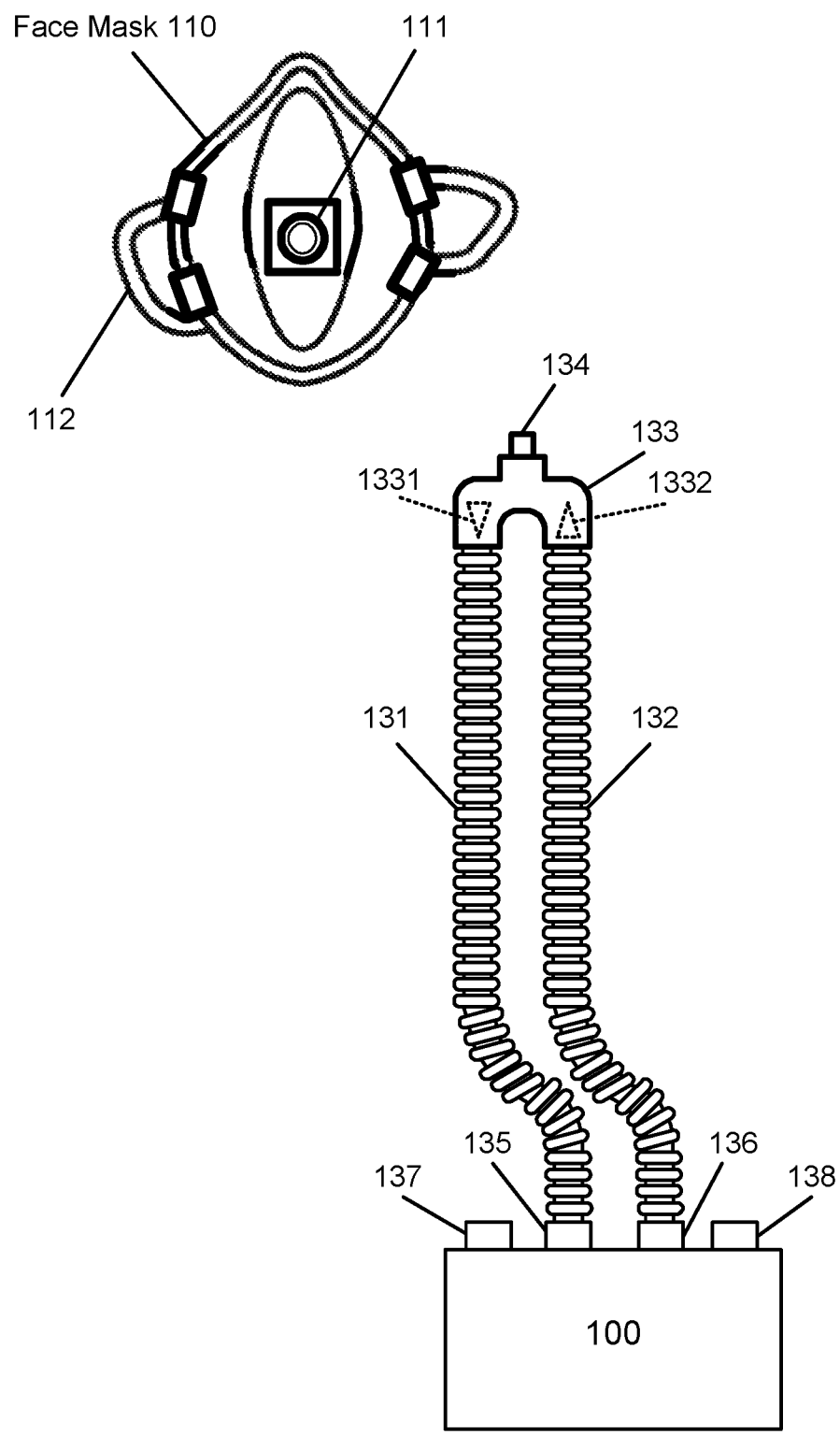
FIG. 3 illustrates a respirator system that includes a portable air filtration and disinfection device and a face mask, according to an embodiment of the present invention.

FIG. 3 illustrates a respirator system that includes a portable air filtration and disinfection device 100 and face mask 110 according to an embodiment of the present invention. The portable air filtration and disinfection device 100 may be connected with face mask 110 in a fluid-communicating manner. As described above, face mask 110 may include tube port 111 and mask strap 112. In some other embodiments, face mask 110 may be replaced by a nasal mask (not shown) or a mouth piece (not shown). Similar to the scenario shown in FIG. 2, portable air filtration and disinfection device 100 may include flexible tubes that form an exhalation branch 131 and an inhalation branch 132 that are coupled with mask 110 respectively. But unlike the scenario shown in FIG. 2, the portable air filtration and disinfection device 100 may not contain branches that connect device 100 with a ventilator.

Similar to braches 101 and 103 of the embodiment shown in FIG. 2, branches 131 and 132 are connected to a Y-connecter 133 that has a connector 134. Connector 134 may be detachably coupled to tube port 111 of mask 110. Tube ends of branches 131 and 132 are connected with tube ports 135 and 136 of device 100, respectively. Tube ports 135 and 136 are coupled with an exhalation duct, e.g., exhalation duct 36, and an inhalation duct, e.g., inhalation duct 46, respectively.

Inside Y-connector 133, there are two one-way directional valves 1331 and 1332. During exhalation, the exhaled air may be released from mask 110 into exhalation branch 131 via valve 1331, while valve 1332 blocks exhalation to inhalation branch 132. For inhalation, the breathing air flows to mask 110 from inhalation branch 132 via valve 1332, while valve 1331 blocks the air from exhalation branch 131. In some other embodiments, one-way directional valves 1331 and 1332 may not be integrated with Y-connector 133. Instead, valves 1331 and 1332 may be discrete devices that may be coupled with branches 101 and 103 separately and individually. For example, in some embodiments, valve 1331 may be inserted between tube port 135 and the tube end of branch 131, and valve 1332 may be inserted between tube port 136 and the tube end of branch 132.

Exhalation branch 131 is connected with an exhalation duct of portable air filtration and disinfection device 100, such as exhalation duct 36, to filter the exhaled air. The filtered exhaled air, after the liquid filtration and the gas filtration, is vented to the outside via an outlet duct, such as outlet duct 35, and an outlet 137 of device 100. Inhalation branch 132 is connected with an inhalation duct of device 100, such as inhalation duct 46. An intake duct of device 100, such as intake duct 45, is connected with an inlet 138 of device 100 where the ambient air may enter. During inhalation, the air flows into device 100 via inlet 138. Then the air is filtered by the liquid filtration and the gas filtration and the filtered air flows to mask 100 via inhalation branch 132.

Hence, by combining the liquid filtration system and the gas filtration system, the respirator system may not only filter harmful particulates and gases from the breathing air and the exhaled air, but also disinfect the breathing air and the exhaled gases. Thus, it protects the surrounding environment by disinfect the exhaled air while ensuring the safety of the breathing air.

Figure 4A:
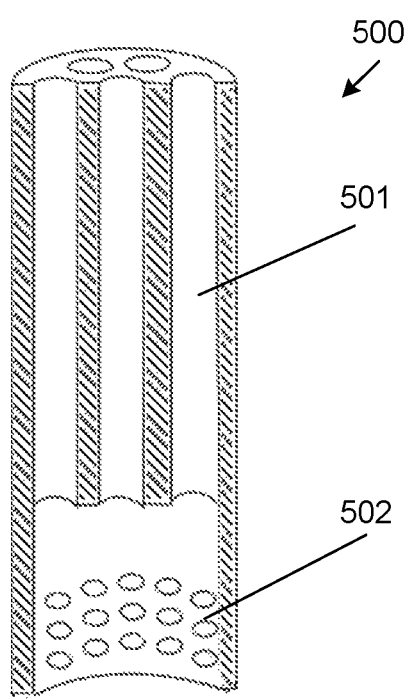
FIGS. 4A and 4B illustrate a cutaway view and a perspective view of an exhalation duct, according to an embodiment of the present invention.
Figure 4B:
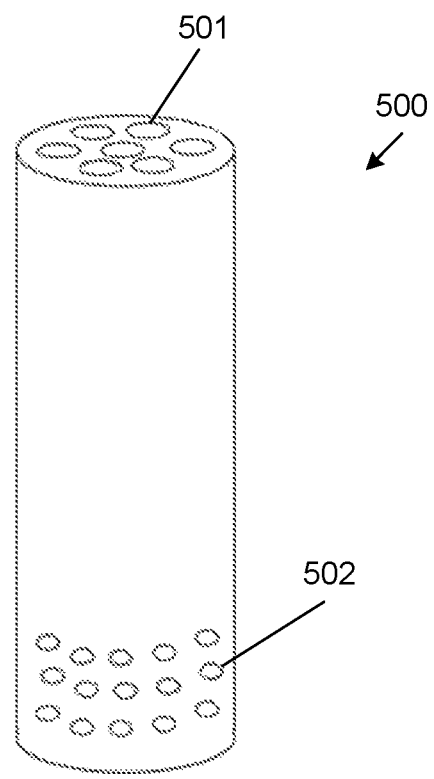

FIGS. 4A and 4B schematically illustrate an exhalation duct 500 for a liquid filter of a respirator system according to embodiments of the present invention. The figures are shown in a cutaway view and a perspective view, respectively. An intake duct of the respirator system may have a similar structure to that of exhalation duct 500. Being different from exhalation duct 36 of the portable air filtration and disinfection device 100 which is a tube with small holes formed on the sidewall close to the bottom of duct 36, duct 500 may have an upper portion and a lower portion. The upper portion of duct 500 may have multiple thin channels 501 where the exhaled air may be passed through from top to bottom. The lower portion of duct 500 may have multiple small holes 502 on the sidewall near the bottom of duct 500. Holes 502 are submerged in a liquid of a liquid filter during operation. The holes are configured sufficiently small in diameter so that air bubbles of sufficiently small dimensions may be generated. When the small holes are submerged in a liquid, such as a disinfection liquid, the holes may be in the liquid with a sufficiently large depth such that the small air bubbles have a sufficient long distance to travel in the liquid for the particulate removal and disinfection process. Duct 500 may be used to replace exhalation duct 36 and/or intake duct 45 of portable air filtration and disinfection device 100, while device 100 is coupled with a face mask or a face mask and a ventilator.

In some embodiments, a filtration device may have an exhalation filter assembly that is similar to aforementioned embodiments and an inhalation filter assembly that is different than the aforementioned embodiments. For example, similar to embodiments described above, the exhalation filter assembly may contain an inhalation gas filter and an exhalation liquid filter, e.g., exhalation gas filter 31 and exhalation liquid filter 32. However, unlike the embodiments described above, the inhalation filter assembly may contain an inhalation gas filter (e.g., inhalation gas filter 41) only, and may not contain an inhalation liquid filter (e.g., inhalation liquid filter 42). In such a scenario, both the exhaled air and inhaled air are filtered, but only the exhaled air may be disinfected when a disinfection liquid is in use. The filtration device may have smaller dimensions and a lighter weight and be suitable for certain hospital environment where there is a need to reduce contamination caused by the exhaled air from patients. Similarly, in some other embodiments, a filtration device may have an exhalation filter assembly that is different than aforementioned embodiments and an inhalation filter assembly that is similar to the aforementioned embodiments. For example, the inhalation filter assembly may contain an inhalation gas filter and an exhalation liquid filter, but the exhalation filter assembly may contain an inhalation gas filter only, and may not contain an inhalation liquid filter.

In some embodiments, portable air filtration and disinfection device 100 may include a first pump, a second pump, and a microcontroller that controls the first and second pumps. The first pump may be connected to exhalation duct 36 and the second pump may be connected to intake duct 45. The first pump may suck the exhaled air into and drive it through exhalation duct 36 during exhalation, and the second pump may suck the breathing air into and drive it through intake duct 45 for inhalation.

In some embodiments, a respirator system may have a compact configuration where, for example, portable air filtration and disinfection device 100 and face mask 110 may be integrated to form a wearable device or a filtering face mask. In some embodiments, face mask 110 may be coupled with a Y-connector that is connected to an exhalation duct and an inhalation duct of device 100, respectively. As such, it is different from the scenario illustrated in FIG. 3 in that face mask 100 and portable air filtration and disinfection device 100 may be integrated and coupled in a fluid-communicating manner without using the long flexible tubes.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

We claim:

1. A portable air filtration and disinfection device for a respirator system, the device comprising:
 a casing having a first chamber and a second chamber, wherein the first chamber and the second chamber are separated by a chamber spacer;
 an inhalation filter assembly housed by the first chamber, the inhalation filter assembly comprising:
  an intake duct for receiving air from an external environment or source,
  an inhalation gas filter for filtering the received air from the external environment or source, and
  an inhalation duct to provide the filtered air to a person for breathing; and
 an exhalation filter assembly housed by the second chamber, the exhalation filter assembly comprising:
  an exhalation duct for receiving air exhaled by the person,
  an exhalation gas filter and an exhalation liquid filter for filtering and disinfecting the received exhaled air from the person, and
  an outlet duct for releasing the filtered and disinfected exhaled air to the external environment or source.

2. The device of claim 1, wherein the inhalation filter assembly further comprises an inhalation liquid filter for filtering and disinfecting the received air from the external environment or source.

3. The device of claim 1, wherein the inhalation gas filter or the exhalation gas filter includes one or more layers of a filtering material.

4. The device of claim 1, wherein the inhalation gas filter or the exhalation gas filter include one or more layers of an adsorption material.

5. The device of claim 1, wherein the exhalation liquid filter comprises a disinfection liquid.

6. The device of claim 1, wherein the inhalation duct and the exhalation are configured to be coupled with a mask.

7. The device of claim 6, wherein the mask is a face mask, a nasal mask, or a mouth piece.

8. The device of claim 1, wherein the inhalation filter assembly further comprises a plurality of first bayonets for fastening the inhalation gas filter and the exhalation filter assembly further comprises a plurality of second bayonets for fastening the exhalation gas filter.

9. The device of claim 1, wherein the intake duct and the outlet duct are configured to be coupled with a ventilator.

10. The device of claim 1, wherein the exhalation duct has a bottom sidewall which comprises a plurality of small holes for generating bubbles of the received exhaled air.

11. A portable air filtration and disinfection device for a respirator system, the device comprising:
- an inhalation filter assembly comprising:
  - an intake duct for receiving air from an external environment or source,
  - an inhalation gas filter for filtering the received air from the external environment or source, and
  - an inhalation duct connected with a mask for providing the filtered air to a person for breathing via the mask;
- an exhalation filter assembly comprising:
  - an exhalation duct connected with the mask for receiving air exhaled by the person via the mask,
  - an exhalation gas filter and an exhalation liquid filter for filtering and disinfecting the received exhaled air from the person, and
  - an outlet duct for releasing the filtered and disinfected exhaled air to the external environment or source; and
- a casing housing the inhalation filter assembly and the exhalation filter assembly.

12. The device of claim 11, wherein the inhalation filter assembly further comprises an inhalation liquid filter for filtering and disinfecting the received air from the external environment or source.

13. The device of claim 11, wherein the intake duct and the outlet duct are coupled with a ventilator.

14. The device of claim 11, wherein the inhalation gas filter or the exhalation gas filter includes one or more layers of a filtering material.

15. The device of claim 11, wherein the inhalation gas filter or the exhalation gas filter include one or more layers of an adsorption material.

16. A portable air filtration and disinfection device for a respirator system, the device comprising:
- a casing having a first chamber and a second chamber, wherein the first chamber and the second chamber are separated by a chamber spacer;
- an inhalation filter assembly housed by the first chamber, the inhalation filter assembly comprising:
  - an intake duct connected with a ventilator for receiving air from the ventilator,
  - an inhalation gas filter for filtering the received air from the ventilator, and
  - an inhalation duct to provide the filtered air to a person for breathing; and
- an exhalation filter assembly housed by the second chamber, the exhalation filter assembly comprising:
  - an exhalation duct for receiving air exhaled by the person,
  - an exhalation gas filter and an exhalation liquid filter for filtering and disinfecting the received exhaled air from the person, and
  - an outlet duct connected with the ventilator for releasing the filtered and disinfected exhaled air to the ventilator.

17. The device of claim 16, wherein the inhalation filter assembly further comprises an inhalation liquid filter for filtering and disinfecting the received air from the ventilator.

18. The device of claim 16, wherein the inhalation duct and the exhalation duct are coupled with a mask.

19. The device of claim 16, wherein the inhalation gas filter or the exhalation gas filter includes one or more layers of a filtering material.

20. The device of claim 16, wherein the inhalation gas filter or the exhalation gas filter include one or more layers of an adsorption material.

* * * * *